(12) United States Patent
Lee et al.

(10) Patent No.: US 7,446,166 B2
(45) Date of Patent: Nov. 4, 2008

(54) PYRROLE DERIVATIVE AND PHOTOSENSITIVE FILM USING THE SAME

(75) Inventors: Hoosung Lee, Seoul (KR); Bongjin Moon, Goyang-si (KR); Heung Cho Ko, Urbana, IL (US); Woonghyun Choi, Chungju-si (KR); Suk-ho Kim, Geoje-si (KR)

(73) Assignee: Industry - University Cooperation Foundation Sogang University, Seoul (KR)

( * ) Notice: Subject to any disclaimer, the term of this patent is extended or adjusted under 35 U.S.C. 154(b) by 550 days.

(21) Appl. No.: 11/254,759

(22) Filed: Oct. 21, 2005

(65) Prior Publication Data

US 2006/0234148 A1 Oct. 19, 2006

(51) Int. Cl.
*C08G 73/06* (2006.01)
*G03G 15/06* (2006.01)
*C07D 471/02* (2006.01)

(52) U.S. Cl. .................. 528/423; 528/424; 528/425; 430/78; 546/37

(58) Field of Classification Search ............. 528/423, 528/424, 425; 430/78; 546/37
See application file for complete search history.

(56) References Cited

OTHER PUBLICATIONS

Bai, et al., "Synthesis and Micropatterning of Semiconducting Polypyrrole Nanofilms by a Two-Step Deposition/Polymerization Process", Advanced Materials, 14, No. 21, Wiley-VCH Verlag GmbH & Co. KGaA, Weinheim, pp. 1546-1549, (Nov. 4, 2002).

Liu, et al., "Self-Assembly and Characterization of A Novel Hydrogen-Bonded Nanostructure", J. Phys. Chem. B, 108, American Chemical Society, pp. 6256-6260, (2004).

Würthner, et al., "Synthesis of Diazadibenzoperylenses and Characterization of Their Structural, Optical, Redox, and Coordination Properties", J. Org. Chem. 67, pp. 3037-3044, (2002).

Klok, et al., "Synthesis and Solid State Properties of Novel Fluorescent Polyester Star Polymers", Macromol. Biosci., vol. 3, No. 12, pp. 729-741, (2003).

Xiao, et al., Dyads and Triads Containing Perylenetetracarboxylic Diimide and Porphyrin: Efficient Photoinduced Electron Transfer Elicited via Both Excited Singlet States, J. Phys. Chem B, 109, pp. 3658-3667, (2005).

Langhals, "Control of the Interactions in Multichromophores: Novel Concepts, Perylene Bis-imides as Components for Larger Functional Units", Helvetica Chimica Acta, vol. 88, pp. 1309-1343, (2005).

(Continued)

*Primary Examiner*—Duc Truong
(74) *Attorney, Agent, or Firm*—Finnegan, Henderson, Farabow, Garrett & Dunner, L.L.P.

(57) ABSTRACT

The present invention relates to pyrrole derivatives and photosensitive film using the same and more particularly, the pyrrole derivatives consist of pyrrole units to allow polymerization chemically and electrochemically and a perylene diimide unit to absorb light so that perylene diimide film can be produced by crosslinking the pyrrole units by irradiation of visible light having wavelengths longer than 500 nm and become insoluble in most solvents. Such perylene diimide films can be widely used in the manufacture of electrical, electronical and optical devices such as photo diodes, solar batteries, liquid crystal displays, and luminescent diodes, etc.

3 Claims, 6 Drawing Sheets

OTHER PUBLICATIONS

Smela, "Microfabrication of PPy microactuators and other conjugated polymer devices", J. Micromech. Microeng. 9, pp. 1-18, (1999).

Scott, et al., "Eletron-spin-resonance studies of pyrrole polymers: Evidence for bipolarons", Physical Review B, vol. 28, No. 4, pp. 2140-2145, (1983).

Yang, et al., "Self-assembled conducting polypyrrole micro/nanotubes", Institute of Physics Publishing, Nanotechnology, 13, pp. 771-773, (2002).

Martre, et al., "Preparation and Properties of a Solube Polypyrrole-Polypyridyl-Ruthenium(II)-Viologen Dyad", J. Phys. Chem. B, 107, pp. 2684-2692, (2003).

You, et al., "Self-Assembly of Ferrocene-Functionalized Perylene Bisimide Bridging Ligands with Pt(II) Corner to Electrochemically Active Molecular Squares", J. Am. Chem. Soc., 125, pp. 9716-9725, (2003).

Bae, et al., "A Water-Soluble and Self-Doped Conducting Polypyrrole Graft Copolymer", Macromolecules, 38, American Chemical Society, pp. 1044-1047, (Jan. 21, 2005).

Choi, et al., "Electrochemical Deposition of a Pyrrole-1-yl Substituted Perylene Diimide for Photoluminescense and Electrochromism", Journal of The Electrochemical Society, vol. 151, (2), pp. E80-E83, (2004).

Ko, et al., "Light-emitting electrochemical cells based on polymide containing perylene and tri(ethylene oxide) moieties", Synthetic Metals, vol. 144, pp. 177-181, (2004).

PYRROLE DERIVATIVE AND PHOTOSENSITIVE FILM USING THE SAME

CROSS REFERENCE TO RELATED APPLICATION

This application claims priority to Korean Patent Application No. 10-2005-0030685, filed on Apr. 13, 2005, the disclosure of which is hereby incorporated by reference in its entirety.

FIELD OF THE INVENTION

The present invention relates to pyrrole derivatives and photosensitive film using the same. More specifically, the present invention relates to novel pyrrole derivatives and the photosensitive film prepared by utilizing the pyrrole derivatives, wherein the pyrrole derivatives comprise both pyrrole units to allow chemical and electrochemical polymerization and a perylene diimide unit to absorb light so that the perylene diimide film can be produced by crosslinking via pyrrole moieties upon irradiating visible light with wavelengths of longer than 500 nm. The crosslinked perylene diimide film prepared in this way is insoluble in most of the common solvents and can be widely used as electrical, electronical and optical elements in the devices such as photodiodes, solar batteries, liquid crystal displays, and luminescent diodes.

BACKGROUND OF THE INVENTION

Patterning technologies have been used in the manufacture of electrical and optical devices using organic films. Especially, the patterning technique typically used in the semiconductor processes is photo-patterning in which the material absorbs light and is then cross-linked or degraded to provide desired patterns. Such methods can be used when the absorption wavelength of the material and the wavelength of the irradiation are overlapped. However, there is a limit in using this method because no cross-linking occurs when the absorption wavelength of the material and wavelength of irradiation differ from each other.

SUMMARY OF THE INVENTION

The invention has been developed to solve the foregoing problems. In an embodiment, the invention provides pyrrole derivatives having pyrrole units to allow chemical and electrochemical polymerization and a perylene diimide unit to absorb light. Thus patterned and insoluble perylene diimide film can be produced by utilizing such pyrrole derivatives by irradiation of visible light having a wavelength of longer than 500 nm.

In another embodiment, the invention provides a photosensitive film prepared by coating and crosslinking the pyrrole derivative.

BRIEF DESCRIPTION OF THE DRAWINGS

The aforementioned aspects and other features of the present invention will be explained in the following detailed description, taken in conjunction with the accompanying drawings, wherein.

DETAILED DESCRIPTION OF THE INVENTION

The present invention is to provide pyrrole derivatives expressed by the following formula 1:

wherein n is an integer of 2 to 20 and m is an integer of 0 to 20.

The present invention is described in detail hereinafter.

The present invention provides pyrrole derivatives having both a pyrrole unit which allows chemical and electrical polymerizations and a perylene diimide unit which absorbs light and photosensitive films obtained by coating the pyrrole derivative on a substrate. The photosensitive film of the present invention is prepared by crosslinking via the pyrrole moieties with visible light having a wavelength of longer than 500 nm and becomes insoluble perylene diimide resin film so that it can be widely used in the manufacture of electrical, electronical and optical elements in the devices such as photodiodes, solar batteries, liquid crystal displays, and luminescent diodes.

When the pyrrole derivative expressed by formula 1 of the present invention is exposed to visible light, an electron in the HOMO level of perylene moiety is excited and an electron of pyrrole transfers to the empty HOMO level of perylene moiety to provide cation radical of pyrrole. The pyrrole radical reacts with other pyrrole units nearby to produce polypyrrole or polypyrrole cross-links. Thus the produced polypyrrole backbone, particularly cross-linked polypyrrole backbone, forms a film insoluble in most of the common organic solvents.

The pyrrole derivative expressed by formula 1 of the present invention has excellent solubility in an organic solvent and can be converted to an insoluble resin upon exposure to light irradiation thus giving more freedom in selection of a solvent for the fabrication of an upper layer in various devices.

The pyrrole derivative expressed by formula 1 of the present invention also has a special feature in its chemical structure that it contains a perylene diimide moiety which has useful optical and electrochemical properties. Therefore, it allows potential applications in such as photodiodes, solar batteries, electrochromic devices, luminescent diodes, liquid crystal displays, etc.

The pyrrole derivative expressed by formula 1 of the present invention provides improved solubility in a variety of solvents due to the phenoxy substituents at position C-1, C-6, C-7, and C-12 of the perylene diimide unit. Such improved solubility is brought by the introduction of phenoxy groups, which increase the steric hinderances between perylene units. Therefore, films of perylene diimide with phenoxy substituents can easily be prepared by spin coating owing to its relatively high solubility.

As the pyrrole derivative expressed by formula 1 of the present invention has a pyrrole unit at the end of each substituent, the pyrrole units can be polymerized easily under irradiation of visible light to form films insoluble in common organic solvents.

The following Scheme 1 and Scheme 2 show brief method for preparing the pyrrole derivatives of formula 1, wherein m=n=3.

Scheme 1

According to Scheme 1, 2,5-dimethyltetrahydrofuran, 3-bromopropylamine hydrobromide (25 g, 114 mM) and sodium acetate (13.24 g, 161.4 mM) were added, stirred for 10 min at 120° C., and then cooled to room temperature. The reaction mixture was then extracted with sodium chloride solution and dichloromethane and the resulting organic layer was collected. After the solvent was evaporated, 3-bromopropyl pyrrole was separated from the residue using column chromatography.

Scheme 2

-continued

(4)

(5)

(6)

(1)

3,4,9,10-Perylenetetracarboxylic dianhydride and butylamine were reacted as shown in Scheme 2 to produce N,N'-bis-n-butyl-3,4,9,10-perylenetetracarboxylic diimide expressed by formula 3. N,N'-Bis-n-butyl-1,6,7,12-tetrachloroperylene-3,4,9,10-tetracaboxylic diimide (compound 4) was synthesized by chlorination of the compound 3 with sulfonyl chloride($SO_2Cl_2$). The compound of formula 4 and 4-butoxyphenol were reacted to produce N,N'-bis-n-butyl-1,6,7,12-tetrakis(4-n-butyloxyphenoxy)perylene-3,4,9,10-tetracarboxylic diimide expressed by formula 5. The compound of formula 5 and boron tribromide were reacted to produce N,N'-bis-n-butyl-1,6,7,12-tetrakis(4-hydroxyphenoxy) perylene-3,4,9,10-tetracarboxylic diimide expressed by formula 6. The compound of formula 6 and 3-bromopropyl pyrrole were reacted to produce the desired product expressed by formula 1.

More details of the present invention will be described with reference to the following examples. The scope of the present invention is not confined within the examples.

EXAMPLE 1

Synthesis of 3-bromopropylpyrrole

Into acetic acid(16.5 mL) charged in a round-bottomed flask were added 2,5-dimethylhydrofuran(15.1 g, 114 mmol), 3-bromopropylamine hydrobromide(25.0 g, 114 mmol), and sodium acetate(13.24 g, 161.4 mmol). After stirring the reaction mixture for 10 min at 120° C., it was cooled to room temperature. The reaction mixture was extracted with sodium chloride solution and dichloromethane. The organic solvent was then removed by evaporation and the residue was purified by column chromatography (silica gel, dichloromethane:hexane=3:1) to obtain colorless liquid.

Yield 33.5% (7.19 g, 38.23 mmol);

$^1$H NMR(500 MHz, CDCl$_3$) δ 6.67(t, J=2.0 Hz, 2H), 6.15 (t, J=2.0 Hz, 2H), 4.07(t, J=6.5 Hz, 2H), 3.31(t, J=6.5 Hz, 2H), 2.25(m, J=6.0 Hz, 2H);

$^{13}$C NMR (125 MHz, CDCl$_3$) δ 120.84, 108.59, 47.21, 34.35, 30.46.

EXAMPLE 2

Synthesis of N,N'-bis-n-butyl-3,4,9,10-perylenetetracarboxylic diimide(formula 3)

3,4,9,10-Perylenetetracarboxylic dianhydride (compound 2) (3.92 g, 10 mmol) was added into a mixture of water(100 mL) and propanol(100 mL). Butylamine(2.93 g, 40 mmol) was added to the mixture dropwise and the reaction mixture was stirred for 12 hours at 80° C. The precipitate produced was filtered and washed with water and methanol and then dried to obtain the compound of formula 3.

Yield 76% (3.82 g, 7.6 mmol).

EXAMPLE 3

Synthesis of N,N'-bis-n-butyl-1,6,7,12-tetrachloroperylene-3,4,9,10-tetracarboxylic diimide (formula 4)

A round-bottom flask was dried in vacuum to remove any remaining moisture and filled with argon gas. N,N'-Bis-n-butyl-3,4,9,10-perylenetetracarboxylic diimide (compound 3) (3.82 g, 7.60 mmol), nitrobenzene (29.2 g, 237 mmol), iodine (0.29 g, 2.28 mmol), and iodobenzene (0.29 g, 1.42 mmol) were added into the round flask. Sulfonyl chloride (SO$_2$Cl$_2$, 6.14 g, 45.5 mmol) was added dropwise for 2 hours at 80° C. while stirring. After the reaction mixture was reacted for 8 hours, methanol (180 mL) was added and stirred for additional 6 hours. The precipitate produced was filtered to obtain the compound of formula 4.

Yield 89% (4.3 g, 6.7 mmol);

$^1$H NMR (500 MHz, CDCl$_3$, r.t.) δ 8.68 (s, 4H), 4.22 (t, 4H), 1.73 (m, 4H), 1.48 (m, 4H), 1.00 (t, 6H);

$^{13}$C NMR (125 MHz, CDCl$_3$, r.t.) δ 162.45, 135.55, 133.12, 131.62, 128.77, 123.44, 40.92, 30.36, 20.51, 14.00.

EXAMPLE 4

Synthesis of N,N'-bis-n-butyl-1,6,7,12-tetrakis(4-n-butyloxyphenoxy)perylene-3,4,9,10-tetracarboxylic diimide (formula 5)

N,N'-bis-n-butyl-1,6,7,12-tetrachloroperylene-3,4,9,10-tetracarboxylic diimide (compound 4) (6.00 g, 9.37 mmol), 4-butyloxyphenol(9.34 g, 56.2 mmol), potassium carbonate (7.77 g, 56.2 mmol), and N-methylpyrrolidinone(200 mL) were added into a round-bottom flask charged with argon gas and the mixture was stirred at 160° C. for 6 hours. After cooling to room temperature, the reaction mixture was stirred while adding hydrochloric acid (2 M, 200 mL) dropwise to obtain black precipitate. The precipitate was filtered, washed with water and methanol, and vacuum-dried. The crude product was purified by flash column chromatography (silica gel, dichloromethane) to obtain the compound of formula 5.

Yield 62.7% (6.81 g, 5.88 mmol);

$^1$H NMR (500 MHz, CDCl$_3$) δ 8.10 (s, 4H), 6.89 (d, J=8.5 Hz, 8H), 6.82 (d, J=8.5 Hz, 8H), 4.10 (t, J=7.5 Hz, 4H), 3.94 (t, J=6.5 Hz, 8H), 1.77 (m, J=7.5 Hz, 8H), 1.64 (m, J=7.5 Hz, 4H), 1.52 (m, J=8.0 Hz, 8H), 1.39 (m, J=8.0 Hz, 4H), 1.00 (t, J=7.0 Hz, 12H), 0.93 (t, J=7.5 Hz, 6H);

$^{13}$C NMR (125 MHz, CDCl$_3$) δ 163.63, 156.85, 156.41, 148.54, 132.99, 122.57, 121.62, 120.00, 119.25, 119.09, 115.95, 68.37, 40.52, 31.52, 30.32, 20.50, 19.44, 14.05, 13.95.

EXAMPLE 5

Preparation of N,N'-bis-n-butyl-1,6,7,12-tetrakis(4-hydroxyphenoxy)perylene-3,4,9,10-tetracarboxylic diimide (formula 6)

While stirring a mixture of dichloromethane(250 mL) and N,N'-bis-n-butyl-1,6,7,12-tetrakis(4-n-butyloxyphenoxy) perylene-3,4,9,10-tetracarboxylic diimide (compound 5) (6.80 g, 5.86 mmol) in a round-bottom flask at room temperature, borontribromide (BBr$_3$, 21.8 g, 87.1 mmol) in dichloromethane (20 mL) was added dropwise. After stirring the mixture for 2 hours, the organic solvent was removed by evaporation. Ice water (200 mL) was added to the residue at 0° C. and methanol(100 mL) was also added. After boiling the mixture for 1 min, the precipitate was filtered and dried at 80° C. to obtain the compound of formula 6.

Yield 94.9% (5.20 g, 5.56 mmol);

$^1$H NMR (500 MHz, DMSO-d$_6$) δ 9.50 (s, 4H), 7.79 (s, 4H), 6.83 (d, J=8.5 Hz, 8H), 6.76 (d, J=8.5 Hz, 8H), 3.93 (t, J=6.5 Hz, 4H), 1.53 (m, J=7.0 Hz, 4H), 1.29 (m, J=7.5 Hz, 4H), 0.87 (t, J=7.5 Hz, 6H);

$^{13}$C NMR (125 MHz, DMSO-d$_6$) δ 162.54, 156.19, 154.51, 145.56, 132.21, 122.14, 118.48, 118.18, 117.26, 116.36, 114.44, 29.48, 19.68, 13.65. (a peak at 40 ppm was overlapped with that of DMSO)

EXAMPLE 6

Synthesis of Pyrrole Derivative(formula 1a)

Into N,N'-bis-n-butyl-1,6,7,12-tetrakis(4-hydroxyphenoxy)perylene-3,4,9,10-tetracarboxylic diimide) (formula 6, 5.02 g, 5.37 mmol) dissolved in DMF (250 mL) were added 3-bromopropylpyrrole (6.06 g, 32.22 mmol) synthesized in Example 1, cesium hydroxide (CsOH) (5.41 g, 32.22 mmol), and tetrabutylammonium iodide (TABI) (0.37 g, 1.0 mmol). After stirring the reaction mixture for 10 hours at room temperature, the product was extracted with dichloromethane and sodium chloride solution. The organic solvent was removed by evaporation and the residue was purified by flash column chromatography (silica gel, MC/methanol, 50/1) followed by recrystallization from dichloromethane/hexane to obtain N,N'-bis-n-butyl-1,6,7,12-tetrakisperylene[4-(3-pyrrole-1-propyloxy)phenoxy]-3,4,9,10-tetracarboxylic diimide expressed by formula 1a.

Yield 50% (3.65 g, 2.68 mmol);

$^1$H NMR (500 MHz, CDCl$_3$) δ8.11 (s, 4H), 6.83 (d, J=9.0 Hz, 8H), 6.81 (d, J=9.0 Hz, 8H), 6.68 (t, J=2.0 Hz, 8H), 6.17 (t, J=2.0 Hz, 8H), 4.13 (t, J=6.5 Hz, 12H), 3.87 (t, J=6.0 Hz, 8H), 2.12 (m, J=6.5 Hz, 8H), 1.65 (m, J=7.5 Hz, 4H), 1.38 (m, J=7.0 Hz, 4H), 0.93 (t, J=7.5 Hz, 6H);

$^{13}$C NMR (125 MHz, DMSO-d$_6$) δ 163.59, 156.76, 155.94, 148.91, 132.99, 122.65, 121.67, 120.94, 120.07, 119.35, 115.97, 108.44, 64.95, 45.15, 40.55, 31.94, 30.34, 20.50, 13.96.

EXPERIMENTAL EXAMPLE 1

Formation of Insoluble Cross-Linked Polymer by Irradiation with Visible Light

After dissolving N,N'-bis-n-butyl-1,6,7,12-tetrakisperylene[4-(3-pyrrole-1-propyloxy)phenoxy]-3,4,9,10-tetracarboxylic diimide synthesized in Example 6 in chloroform to make concentration of 15 mg/mL, the solution was filtered through a 0.45-μm membrane filter to remove any fine dust particles and other insoluble contaminants.

After cleaning ITO-coated glass substrate, thin film of compound 1 was coated by spin coating the prepared solution on the glass substrate at 1500 rpm.

Figure 1:
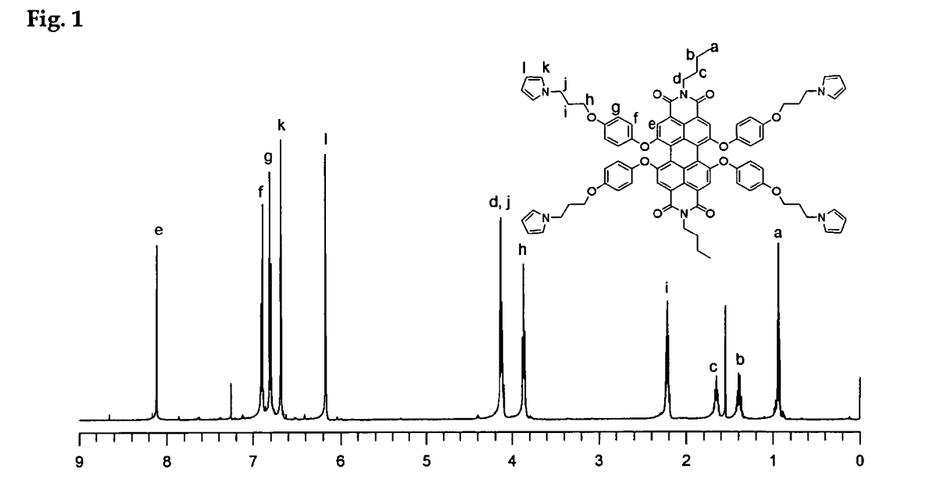
FIG. 1 is the $^1$H-NMR spectrum of the pyrrole derivative expressed by formula 1a prepared in Example 6.
Figure 2A:
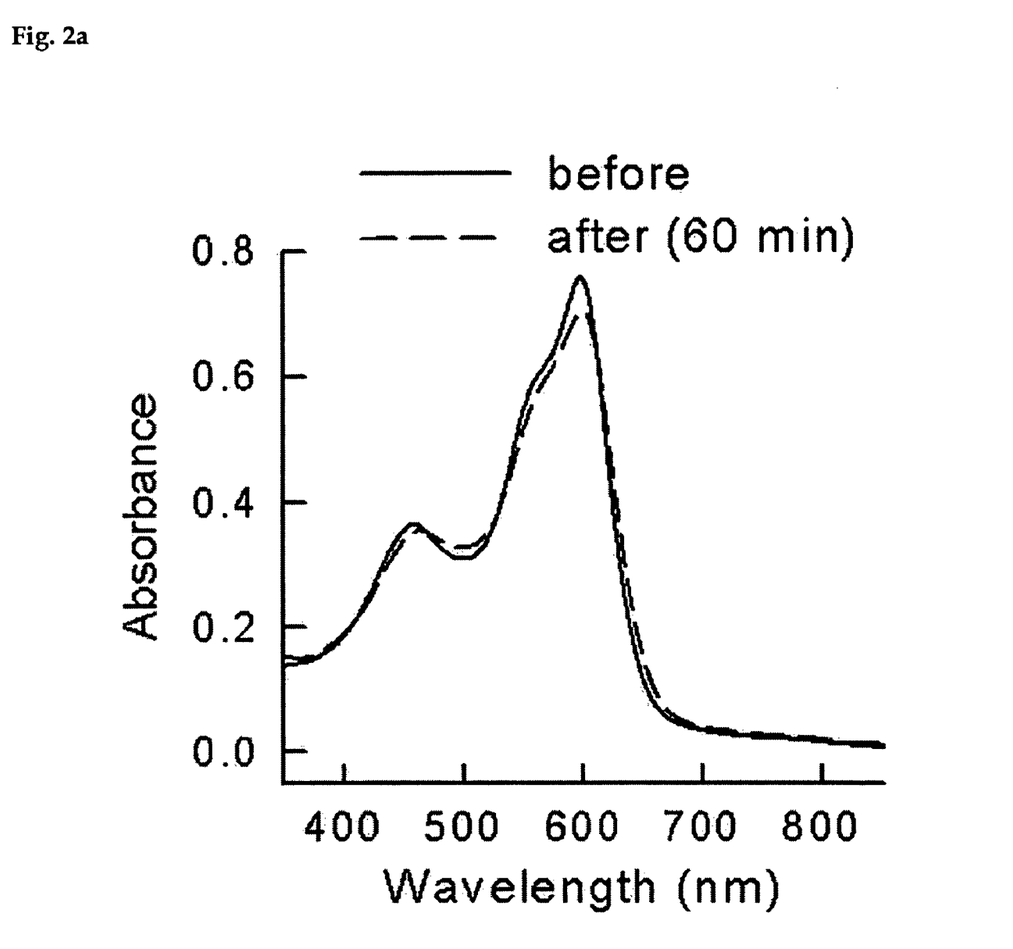
FIG. 2a is the UV-Visible spectrum before and after light irradiation to the film prepared by coating the pyrrole derivative of formula 1.

In order to confirm the formation of insoluble film by photo-crosslinking, the absorbance of the film was measured in the ultraviolet-visible region before and after light irradiation. The result was shown in FIG. 2a. After recording the UV-Visible spectrum of the coated film, it was irradiated with visible light with wavelengths longer than 500 nm. Xe-lamp was used as a light source and a filter was used to select wavelengths longer than 500 nm so that electrons only in the perylene diimide moiety can be excited without exciting those in the pyrrole moiety. The irradiation time varied from 1 min to 60 min. After light irradiation, the film was washed with chloroform to remove soluble species which was not cross-linked and the absorbance in the ultraviolet-visible region was measured.

Figure 2B:
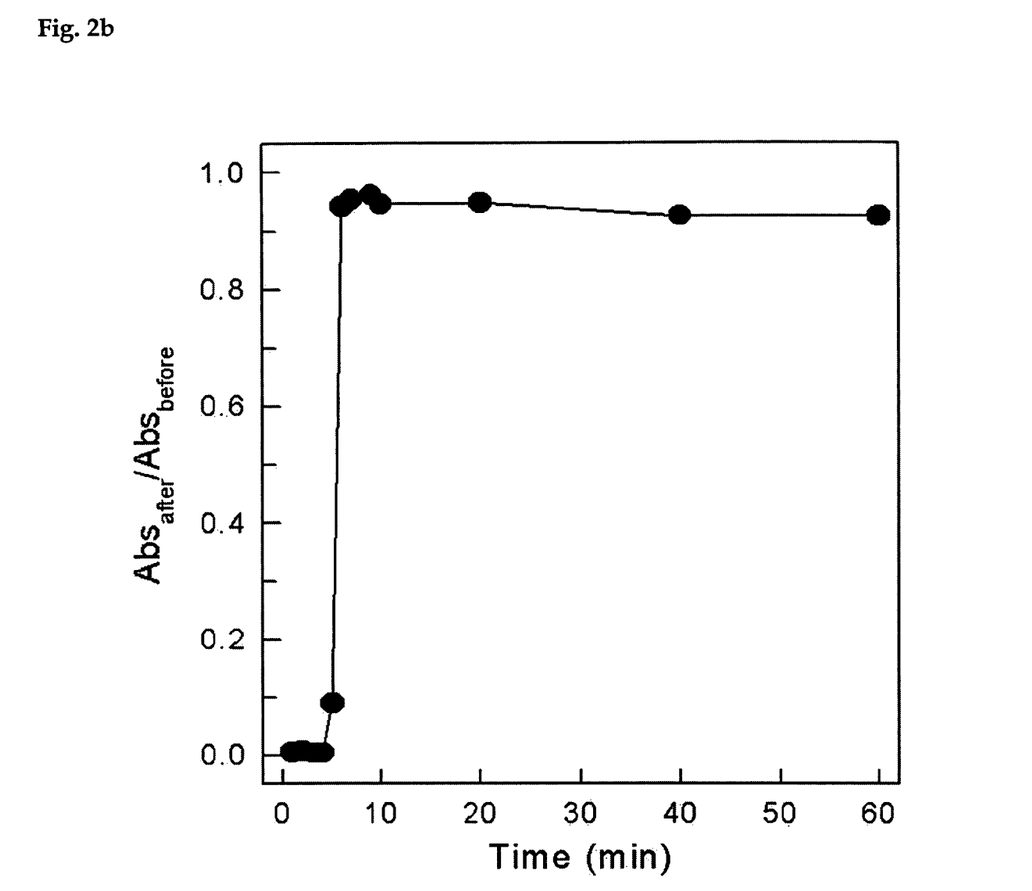
FIG. 2b is a graph illustrating the formation of insoluble film through photo-crosslinking with light irradiation.

Abs$_{before}$ in FIG. 2b is the absorbance of the film before the irradiation of light measured at the wavelength of maximum absorption in the UV-Visible region and Abs$_{after}$ is the absorbance of the film measured after the irradiation of light and dissolving out the soluble portion with chloroform. The Abs$_{after}$/Abs$_{before}$ ratio is nearly 0 up to 4 min of irradiation time but jumps up rapidly to 0.95 after 6 min, i.e. 95% of the film transformed into insoluble form by light irradiation. This indicates that the film formed by photo-crosslinking is not soluble in the solvent.

EXPERIMENTAL EXAMPLE 2

Confirmation of Cross-Linking via FT-IR Spectrum

Figure 3:
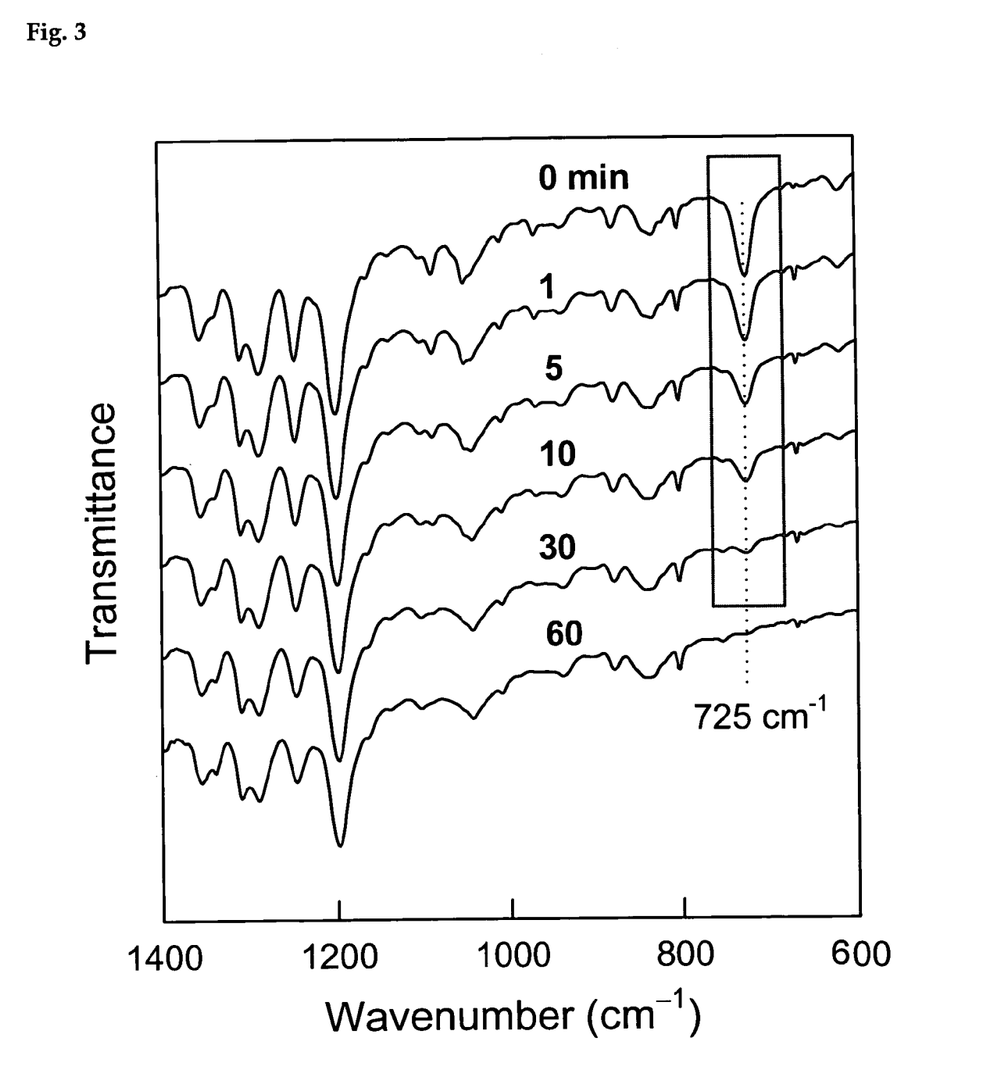
FIG. 3 is change in IR spectrum according to irradiation time of visible light to the pyrrole derivative expressed by formula 1.

Film of compound 1 was formed on potassium bromide (KBr) window substrate by spin-coating the solution prepared in Experimental Example 1 as described above. FIG. 3 shows the change in IR spectrum with the irradiation time.

Although there was almost no change in IR spectrum with irradiation of visible light, it was noted that the peak at 725 cm$^{-1}$ which was clearly visible before the irradiation disappeared gradually as the irradiation time increased. The peak at 725 cm$^{-1}$ is well known as C—H bending vibration in the pyrrole ring. The disappearance of this peak evidences that polymerization occurred via the pyrrole moieties by light irradiation.

EXPERIMENTAL EXAMPLE 3

Test for Uniformity of the Film Surface Using SEM

Figure 4A:
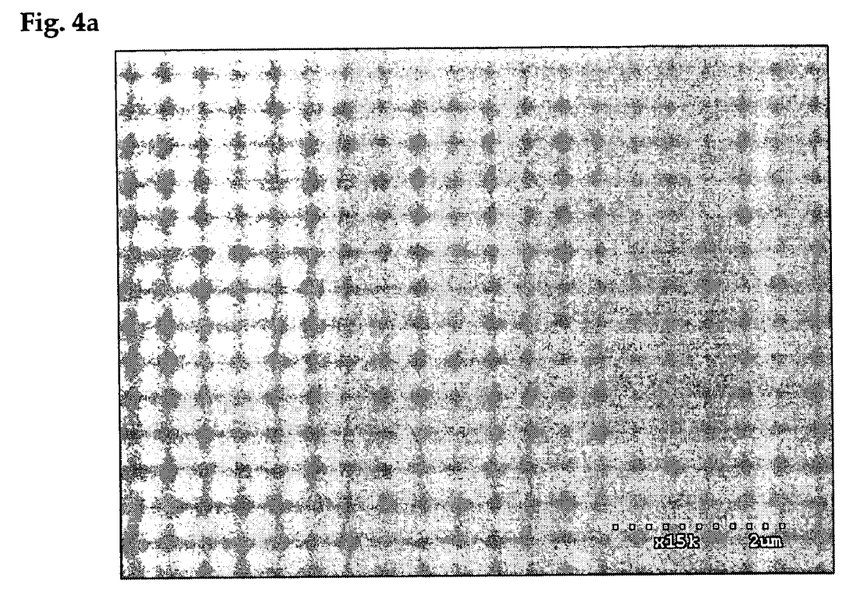
FIG. 4a is a SEM picture before light irradiation to the film prepared by spin coating with the pyrrole derivative expressed by formula 1 on ITO coated substrate.
Figure 4B:
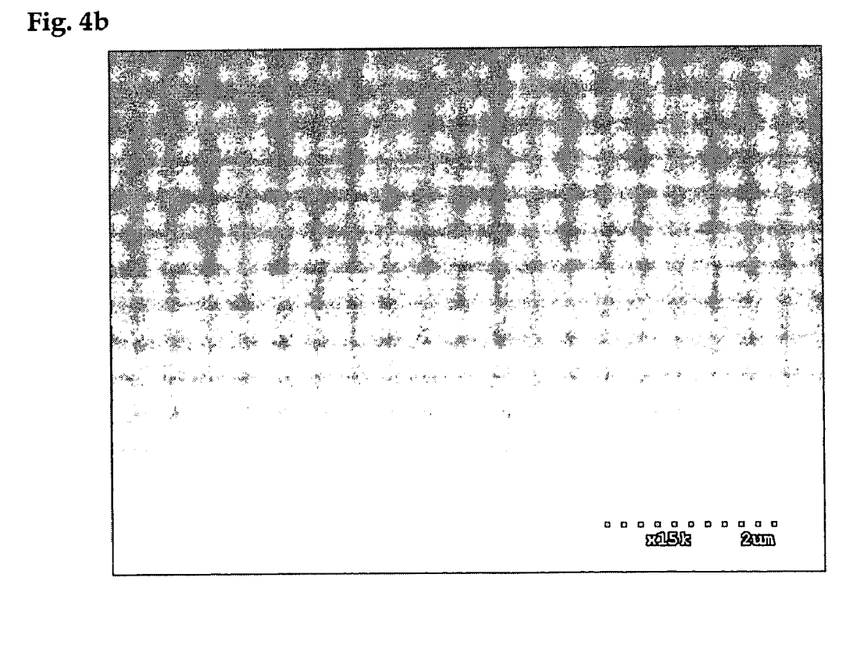
FIG. 4b is a SEM picture of the film after light irradiation for 1 hour and washing off the soluble portion with chloroform.

The SEM pictures of the film surface taken before and after irradiation with UV-visible light are shown in FIGS. 4a and 4b. FIG. 4a shows the SEM picture of the film prepared by spin coating at a rate of 1500 rpm on ITO coated glass with solution of N,N'-bis-n-butyl-1,6,7,12-tetrakisperylene[4-(3-pyrrole-1-propyoxy)-penoxy]-3,4,9,10-tetracarboxylic diimide prepared in Example 1 and FIG. 4b is the SEM picture of the same film as in FIG. 4a after irradiation of light with wavelengths longer than 500 nm for 1 hour and washing with chloroform.

Both pictures taken before and after light irradiation shows very smooth and uniform film surface without any defect.

EXPERIMENTAL EXAMPLE 4

Formation of Pattern via Photo-Cross-Liking

Figure 5:
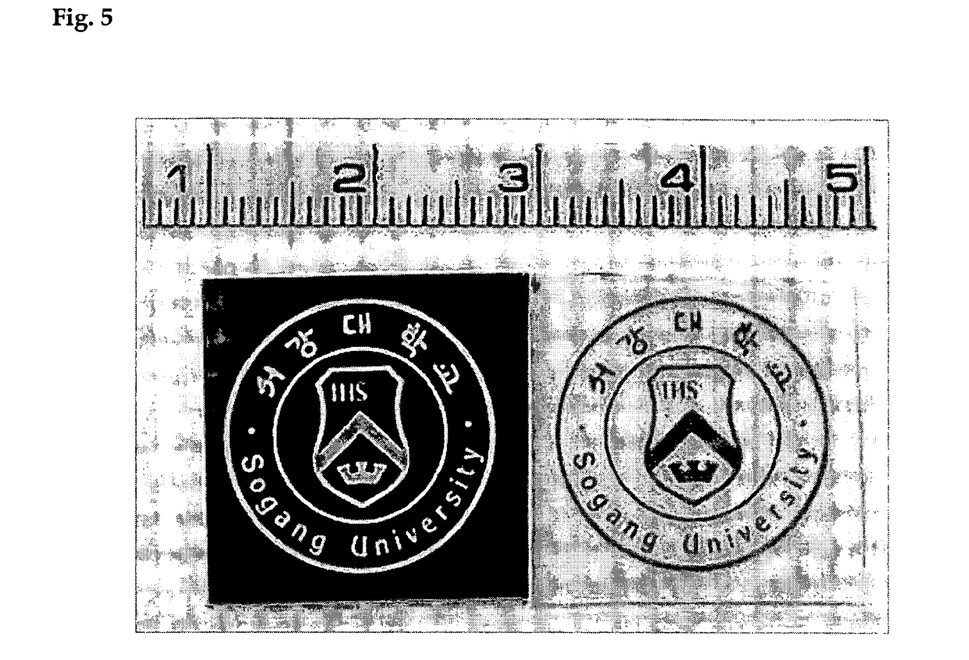
FIG. 5 is a patterned picture of the pyrrole derivative film of formula 1a with irradiation of visible light on OHP film, wherein left picture is the mask for patterning and right one is a patterned perylene diimide film.

FIG. 5 is a picture of the patterned film prepared by spin coating the solution of N,N'-bis-n-butyl-1,6,7,12-tetrakisperylene[4-(3-pyrrole-1-propyoxy)-penoxy]-3,4,9,10-tetracarboxylic diimide prepared in Example 1 on ITO coated glass at 1500 rpm. The picture on left side in FIG. 5 is the negative mask and the one on right side is the patterned perylene diimide film which shows a very clear and sharp image of the mask.

The pyrrole derivatives and the photosensitive film prepared from such pyrrole derivatives of the present invention consist of both pyrrole units and a perylene diimide unit. The pyrrole units can be polymerized chemically or electrochemically. The perylene diimide unit can absorb light and the absorbed light energy is transferred to the pyrrole units and used to polymerize the pyrrole units to form insoluble perylene diimide film. The insoluble film of perylene diimide can be formed by photo-crosslinking the pyrrole derivative (compound 1) with exposure of visible light having a wavelength of longer than 500 nm. Such perylene diimide film can be widely used in the fabrication of electrical, electronical and optical devices such as photo-diodes, solar batteries, liquid crystal displays, and luminescent diodes.

The pyrrole derivatives of the present invention have excellent solubility in various organic solvents and can be polymerized with irradiation of visible light. When the pyrrole derivatives are irradiated with visible light, they can readily form a film which is insoluble in most of the common organic solvents and patterns of insoluble perylene diimide film can be formed by irradiating selective areas. The pyrrole derivatives of the present invention and the insoluble perylene diimide film prepared from the same compound have a relatively wide scope of applications in the area of information and communication technologies as well as in display and solar energy conversion technologies.

While the foregoing description represent various embodiments of the present invention, it will be appreciated that the foregoing description should not be deemed limiting since additions, variations, modifications and substitutions may be made without departing from the spirit and scope of the present invention. It will be clear to one of skill in the art that the present invention may be embodied in other forms, structures, arrangements, and proportions and may use other elements, materials and components. The present disclosed embodiments are, therefore, to be considered in all respects as illustrative and not restrictive, the scope of the invention being indicated by the appended claims and not limited to the foregoing description.

What is claimed is:

1. A pyrrole derivative expressed by the following formula 1:

wherein n is an integer of 2 to 20, and m is an integer of 0 to 20.

2. A photosensitive film by utilizing pyrrole derivative expressed by the following formula 1:

wherein n is an integer of 2 to 20, and m is an integer of 0 to 20.

3. In claim 2, said photosensitive film is an insoluble film manufactured via crosslinking of the pyrrole derivative expressed by the above formula 1.

* * * * *